United States Patent
Kitaoka et al.

(10) Patent No.: US 11,826,072 B2
(45) Date of Patent: Nov. 28, 2023

(54) MEDICAL DEVICE, METHOD FOR CONTROLLING ROTATION OF MEDICAL DEVICE, AND ROTATION CONTROLLER

(71) Applicant: TERUMO KABUSHIKI KAISHA, Tokyo (JP)

(72) Inventors: Takashi Kitaoka, Hadano (JP); Masaomi Imai, Kofu (JP); Kazuaki Kanamoto, Hadano (JP); Yuki Masubuchi, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 315 days.

(21) Appl. No.: 16/831,029

(22) Filed: Mar. 26, 2020

(65) Prior Publication Data
US 2020/0222076 A1  Jul. 16, 2020

Related U.S. Application Data

(63) Continuation of application No. PCT/JP2018/035315, filed on Sep. 25, 2018.

(30) Foreign Application Priority Data

Oct. 4, 2017  (JP) .................................. 2017-194059

(51) Int. Cl.
*A61B 17/3207* (2006.01)
*A61B 17/00* (2006.01)

(52) U.S. Cl.
CPC ............... *A61B 17/320758* (2013.01); *A61B 17/320725* (2013.01); *A61B 2017/00398* (2013.01);
(Continued)

(58) Field of Classification Search
CPC ................. A61B 17/22; A61B 17/221; A61B 17/320758; A61B 17/320725
See application file for complete search history.

(56) References Cited

U.S. PATENT DOCUMENTS

| 5,766,191 A | 6/1998 | Trerotola |
| 2002/0165567 A1* | 11/2002 | Shiber ............ A61B 17/320758 604/164.13 |

(Continued)

FOREIGN PATENT DOCUMENTS

| CN | 203841754 U | 9/2014 |
| CN | 105310745 A | 2/2016 |

(Continued)

OTHER PUBLICATIONS

An English Translation of the International Search Report (Form PCT/ISA/210) and the Written Opinion of the International Searching Authority (Form PCT/ISA/237) dated Dec. 4, 2018, by the Japan Patent Office in Corresponding International Application No. PCT/JP2018/035315. (6 pages).

(Continued)

*Primary Examiner* — Tuan V Nguyen
(74) *Attorney, Agent, or Firm* — BUCHANAN INGERSOLL & ROONEY PC (57) ABSTRACT

A medical device is disclosed that can effectively destroy an object in a biological lumen, a method for controlling rotation of the medical device, and a rotation controller. The medical device to be inserted into a biological lumen to destroy a thrombus in the biological lumen includes a long shaft portion that is rotationally driven, a drive unit that rotates the shaft portion, a breaking member that is provided at a distal portion of the shaft portion and is rotatable, and a control unit that controls the rotation of the drive unit, in which the control unit controls the drive unit to repeat the (Continued)

rotation while interposing a stop of the rotation between rotations of the drive unit.

22 Claims, 8 Drawing Sheets

(52) U.S. Cl.
CPC .............. *A61B 2017/00867* (2013.01); *A61B 2017/320733* (2013.01); *A61B 2217/005* (2013.01)

(56) References Cited

U.S. PATENT DOCUMENTS

| | | | | |
|---|---|---|---|---|
| 2007/0239140 | A1* | 10/2007 | Chechelski | A61B 17/320758 606/1 |
| 2012/0130410 | A1* | 5/2012 | Tal | A61B 17/320758 606/159 |
| 2014/0207052 | A1 | 7/2014 | Tal et al. | |
| 2015/0164541 | A1* | 6/2015 | Shiber | A61B 17/320758 604/35 |
| 2016/0120570 | A1* | 5/2016 | Kobayashi | A61F 2/013 606/166 |
| 2016/0270813 | A1 | 9/2016 | Chida | |
| 2016/0278805 | A1* | 9/2016 | Hatta | A61B 17/320725 |
| 2017/0224364 | A1 | 8/2017 | Imai et al. | |
| 2017/0238960 | A1 | 8/2017 | Hatta et al. | |
| 2017/0252058 | A1 | 9/2017 | Bar-Cohen et al. | |
| 2019/0000500 | A1 | 1/2019 | Masubuchi et al. | |
| 2019/0175212 | A1 | 6/2019 | Kitaoka et al. | |

FOREIGN PATENT DOCUMENTS

| | | |
|---|---|---|
| WO | 2017/151178 A1 | 9/2017 |
| WO | 2017154749 A1 | 9/2017 |
| WO | 2017154909 A1 | 9/2017 |
| WO | 2018038017 A1 | 3/2018 |

OTHER PUBLICATIONS

International Search Report (with English translation) and Written Opinion issued in International Patent Application No. PCT/JP2018/035315 dated Sep. 5, 2018, 7 pages (Dec. 4, 2018).

The extended European Search Report dated Jun. 9, 2020, by the European Patent Office in corresponding European Patent Application No. 18864930.5-1113. (31 pages).

Office Action (The First Office Action) dated Nov. 3, 2022, by the State Intellectual Property Office of People's Republic of China in corresponding Chinese Patent Application No. 201880055689.4 and an English translation of the Office Action. (15 pages).

* cited by examiner

MEDICAL DEVICE, METHOD FOR CONTROLLING ROTATION OF MEDICAL DEVICE, AND ROTATION CONTROLLER

CROSS-REFERENCES TO RELATED APPLICATIONS

This application is a continuation of International Application No. PCT/JP2018/035315 filed on Sep. 25, 2018, which claims priority to Japanese Patent Application No. 2017-194059 filed on Oct. 4, 2017, the entire content of both of which is incorporated herein by reference.

TECHNICAL FIELD

The present disclosure generally relates to a medical device used to effectively destroy an object in a biological lumen, a method for controlling rotation of the medical device, and a rotation controller.

BACKGROUND DISCUSSION

If a thrombus (i.e., blood clot) forms in a biological lumen, the thrombus should be removed promptly. As a symptom in which a thrombus is formed in a biological lumen, for example, deep vein thrombosis in which a thrombus is formed in a deep vein such as a femoral vein or a popliteal vein is exemplified. As a method for treating deep vein thrombosis, methods include inserting a long tubular body of a medical device into a blood vessel, injecting a drug such as a thrombolytic agent into an embolus (or a thrombus), and dissolving the thrombus to remove the thrombus.

Treatment methods in which a drug is injected to remove a thrombus can involve side effects such as bleeding. For this reason, a treatment method has been proposed in which a member made of a wire provided at the distal portion of a shaft inserted into a blood vessel is rotated to mechanically destroy an embolus (thrombus or the like) with which the member comes in contact the to increase the patency rate (rate of a region that is not blocked to a cross section of the blood vessel) (for example, see U.S. Pat. No. 5,766,191). As a result, a drug is not necessary or the amount of drug can be reduced.

When a thrombus in a lumen such as a blood vessel is destroyed by a rotating structure, the embolus from the thrombus floating in the lumen rotates together with the rotating structure. For this reason, it can be difficult to destroy the embolus floating in the lumen.

SUMMARY

A medical device is disclosed that can effectively destroy an object in a biological lumen. In addition, a method for controlling rotation of the medical device and a rotation controller are disclosed.

In accordance with an aspect, a medical device is disclosed, which can be inserted into a biological lumen to effectively destroy an object in the biological lumen including a long shaft portion that is rotationally driven, a drive unit that rotates the shaft portion, a breaking member that is provided at a distal portion of the shaft portion and is rotatable, and a control unit that controls the rotation of the drive unit, in which the control unit controls the drive unit to repeat the rotation while interposing a stop of the rotation between rotations of the drive unit.

In accordance with another aspect, a method is disclosed for controlling rotation of a medical device provided with a long shaft portion that is rotationally driven by a drive unit, and a breaking member provided at a distal portion of the shaft portion to destroy an object in a biological lumen, the method include rotating the shaft portion by the drive unit, stopping the rotation of the drive unit, and rotating the drive unit again.

In accordance with a further aspect, a rotation controller of a medical device provided with a long shaft portion configured to be rotationally driven is disclosed, the rotation controller including a drive unit configured to rotate the shaft portion, and a control unit configured to control the rotation of the drive unit, in which the control unit controls the drive unit to repeat the rotation while interposing a stop of the rotation between rotations of the drive unit.

Since the medical device and the method for controlling the rotation of the medical device configured as described above rotate the breaking member while interposing a stop between rotations of the medical device, it is possible to effectively create a state in which the relative speed between the object and the breaking member, which rotate by receiving the force from the breaking member, is relatively large. Therefore, a high shear stress can be applied to the object to be destroyed by the breaking member, and the object can be rather effectively destroyed.

The rotation controller of the medical device configured as described above can effectively create a state in which the relative speed between the shaft portion and an object that rotates by receiving a force from the shaft portion or a drug such as a thrombolytic agent is relatively large.

BRIEF DESCRIPTION OF THE DRAWINGS

FIGS. 3A and 3B are graphs showing an operation of the medical device, wherein FIG. 3A shows rotation speed with respect to revolutions, and FIG. 3B shows a current supplied to a drive unit with respect to the revolutions.

FIGS. 5A and 5B are cross-sectional views showing a state inside a blood vessel, wherein FIG. 5A shows a state in which the medical device is inserted into a blood vessel, and FIG. 5B shows a state in which the breaking member of the medical device is exposed in the blood vessel.

FIGS. 6A and 6B are cross-sectional views showing a state inside a blood vessel, wherein FIG. 6A shows a state in which a thrombus is destroyed by the breaking member in a contracted state, and FIG. 6B shows a state in which the thrombus is destroyed by the breaking member in an expanded state.

FIGS. 7A-7D are cross-sectional views showing the breaking member rotating in the thrombus, wherein FIG. 7A shows a state in which the breaking member is rotating, FIG. 7B shows a state in which where the breaking member is stopped, FIG. 7C shows a state in which the breaking member is rotating in the opposite direction, and FIG. 7D shows a state in which the breaking member is stopped again.

FIGS. 8A and 8B are cross-sectional views showing the breaking member rotating inside the thrombus, wherein FIG. 8A shows a state in which the breaking member is rotating in a protruding direction of a projection portion, and FIG. 8B shows a state in which the breaking member is expanded.

FIGS. 9A and 9B are cross-sectional views showing the breaking member rotating inside the thrombus, wherein FIG. 9A shows a state in which the breaking member is rotating in a direction opposite to the protruding direction of the projection portion, and FIG. 9B shows a state in which the breaking member is contracted.

FIGS. 10A and 10B are graphs showing another example of the operation of the medical device, wherein FIG. 10A shows rotation speed with respect to revolutions, and FIG. 10B shows a current supplied to a drive unit with respect to the revolutions.

FIGS. 11A and 11B are graphs showing still another example of the operation of the medical device, wherein FIG. 11A shows rotation speed with respect to revolutions, and FIG. 11B shows a current supplied to a drive unit with respect to the revolutions.

FIGS. 12A and 12B are graphs showing still another example of the operation of the medical device, wherein FIG. 12A shows rotation speed with respect to revolutions, and FIG. 12B shows a current supplied to a drive unit with respect to the revolutions.

DETAILED DESCRIPTION

Set forth below with reference to the accompanying drawings is a detailed description of embodiments of a medical device used to effectively destroy an object in a biological lumen, a method for controlling rotation of the medical device, and a rotation controller representing examples of the inventive medical device used to destroy an object in a biological lumen, the method for controlling rotation of the medical device, and the rotation controller. The dimensions or scales on the drawings may be exaggerated or different from actuality/reality for convenience of description and illustration.

A medical device 10 according to the present embodiment is inserted into a blood vessel in deep vein thrombosis, and is used for a treatment for destroying and removing a thrombus. In the present specification, the side of the device to be inserted into a blood vessel is referred to as "distal side", and the hand-side for operation is referred to as "proximal side". Note that, the object to be removed is not necessarily limited to a thrombus, and may be any object that can be present in a biological lumen.

Figure 1:
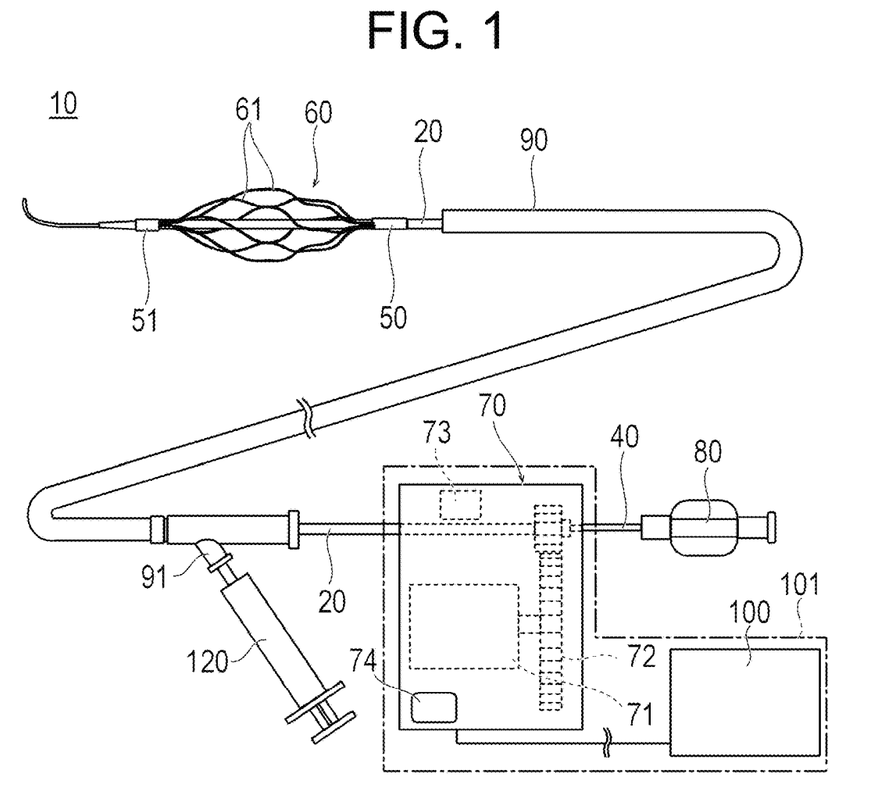
FIG. 1 is a plan view showing a medical device according to an embodiment.

As shown in FIG. 1, the medical device 10 includes a long shaft portion 20 that is rotationally driven, an outer sheath 90 that can accommodate the shaft portion 20, a slide portion 50 that can slide with respect to the shaft portion 20, and a breaking member 60 that is rotated by the shaft portion 20. The medical device 10 further includes a rotation operation unit 70 for rotating the shaft portion 20, a guide wire tubular body 40 into which a guide wire can be inserted, and a hub 80 provided at a proximal end portion of the guide wire pipe body 40.

The proximal end portion of the shaft portion 20 is located in the rotation operation unit 70. The shaft portion 20 can be reciprocated (i.e., rotates in one direction and then rotates in an opposite direction) along the circumferential direction by the rotation operation unit 70. However, the shaft portion 20 is not limited to the one that reciprocates, and may be one that rotates in one direction.

The guide wire tubular body 40 is provided in the hollow interior of the shaft portion 20 from the distal end portion to the hub 80. The guide wire tubular body 40 has a guide wire lumen into which a guide wire can be inserted.

The outer sheath 90 is disposed coaxially outside the shaft portion 20. The lumen of the outer sheath 90 not only accommodates the breaking member 60, but also has a function as an aspiration lumen that generates an aspiration force when in a negative pressure state. The proximal end portion of the outer sheath 90 branches into a Y-shape. In one of the branches, the shaft portion 20 extends to the rotation operation unit 70. The other branch is a bypass 91 to which a syringe 120 can be connected. By connecting the syringe 120, the lumen of the outer sheath 90 can be aspirated and brought into a negative pressure state. Further, by connecting the syringe 120 to the bypass 91, for example, a thrombolytic agent can be injected from the syringe 120 into the lumen of the outer sheath 90.

Figure 2:
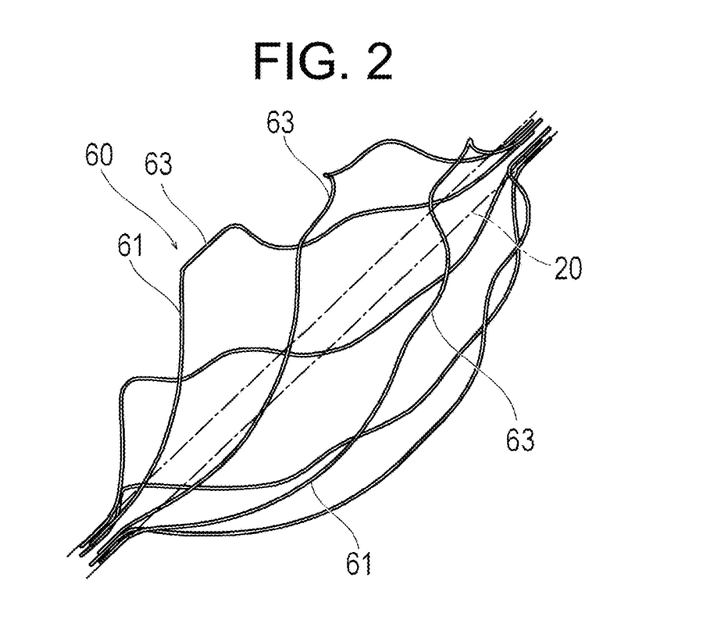
FIG. 2 is a perspective view showing a breaking member of the medical device.

The breaking member 60 is provided at a distal portion of the shaft portion 20. The breaking member 60 includes a plurality of (for example, six (6) wires in the present embodiment) wires 61. Each wire 61 is three-dimensionally curved (i.e., having a three-dimensional shape). Note that, the number of wires 61 is not particularly limited. Each wire 61 is twisted in the same circumferential direction along the axial direction of the shaft portion 20. The proximal end portion of each wire 61 is fixed to the slide portion 50, and wherein the slide portion 50 is slidable with respect to the shaft portion 20. The distal end portion of each wire 61 is fixed to a fixing portion 51 and wherein the fixing portion 51 is fixed to the shaft portion 20. The fixing positions of the respective wires 61 with respect to the fixing portion 51 and the slide portion 50 are arranged in the circumferential direction. Further, the substantial center portions of the wires 61 in the axial direction in which the wires curve are arranged in the circumferential direction at a position away from the shaft portion 20 in the radial direction. Accordingly, an entirety of the breaking member 60 can be uniformly expanded in the circumferential direction. When the shaft portion 20 rotates, the breaking member 60 rotates along with the shaft portion. Therefore, it is possible to break a thrombus in a blood vessel or agitate the broken thrombus (i.e., embolism). Each wire 61 has a projection portion 63 that is three-dimensionally curved and protrudes radially outward when viewed from the front surface and on the same side in the circumferential direction (i.e., the shape of each wire when viewed from the front surface is the same). Note that, each wire 61 may not have the projection portion 63. The breaking means, for example, crushing an object with a structure, and the shape of the structure, the method of crushing, the degree of crushing, the range to be crushed, the shape of the crushed object, and the like are not limited.

The wire 61 constituting the breaking member 60 can be formed of a relatively flexible thin metal wire. In accordance with an embodiment, the breaking member 60 is housed inside the outer sheath 90 until the shaft portion 20 is inserted into a target site. When accommodating the wire 61 in the outer sheath 90, the outer sheath 90 is moved to the distal side with respect to the shaft portion 20, and the distal end portion of the outer sheath 90 is pressed against the proximal portion of the breaking member 60. Accordingly, the slide portion 50 moves to the proximal side along the shaft portion 20, and the wire 61 is reduced in diameter and accommodated inside the outer sheath 90. When the outer sheath 90 is moved to the proximal side with respect to the shaft portion 20 after inserting the shaft portion 20 to a target site in the blood vessel, the breaking member 60 is exposed outside the outer sheath 90 and expands by its own elastic force. At this time, the slide portion 50 moves to the distal side along the shaft portion 20.

The wire(s) 61 of the breaking member 60 is preferably made of a material having shape memory so that it can be elastically deformed. The constituent material of the wire 61 is preferably, for example, a shape memory alloy to which a shape memory effect or superelasticity is imparted by heat treatment, stainless steel, or the like. As the shape memory alloy, a Ni—Ti based alloy, a Cu—Al—Ni based alloy, a Cu—Zn—Al based alloy, or a combination of a Ni—Ti based alloy, a Cu—Al—Ni based alloy, and/or a Cu—Zn—Al based alloy is suitable.

The rotation operation unit 70 includes, as shown in FIG. 1, a drive unit 71 (i.e., a motor) connected to a power supply, a gear unit 72 that links the drive unit 71 with the shaft portion 20, a tachometer 73, and a switch 74. The switch 74 is a part for turning the operation of the drive unit 71 on or off. By rotating the drive unit 71, the shaft portion 20 rotates in the circumferential direction. The tachometer 73 measures the rotation speed of the shaft portion 20. The power supply connected to the drive unit 71 can be, for example, a facility power supply or a battery. The gear ratio of the gear unit 72 can be appropriately set.

The control unit 100 controls the rotation of the drive unit 71. The control unit 100 includes a central processing unit (CPU) and a storage circuit, and is connected to the drive unit 71. The control unit 100 may be connected to an interface such as a keyboard, a mouse, and a monitor. The control unit 100 can be, for example, a computer or a dedicated device. The storage circuit stores a program executed by the control unit 100 and various parameters.

The control unit 100 controls the current supplied to the drive unit 71 so that the breaking member 60 has a predetermined rotation speed. The control unit 100 receives a signal indicating the rotation speed of the shaft portion 20 from the tachometer 73. Note that, the control unit 100 may receive a signal indicating the rotation speed of the drive unit 71 from the drive unit 71 and convert the signal into the rotation speed of the shaft portion 20.

Figures 3A, 3B:
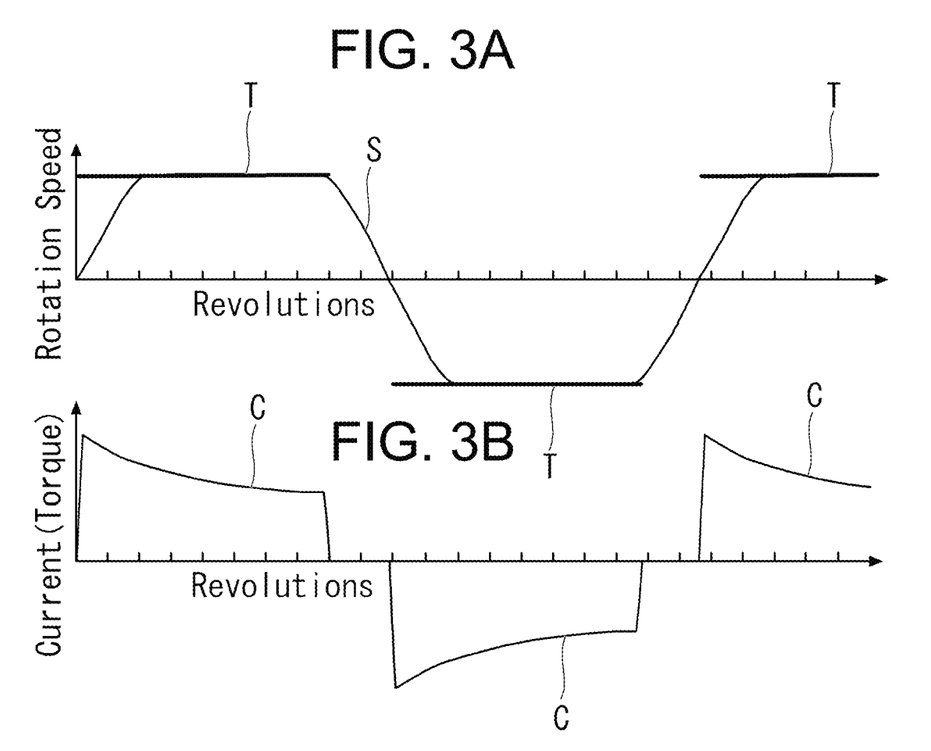

As shown in FIG. 3A, the control unit 100 controls the current C input to the drive unit 71 such that the rotation speed S of the shaft portion 20 coincides with the target rotation speed T. The target rotation speed T is set in advance and stored in the storage circuit. The absolute value of the target rotation speed T with respect to the revolutions of the shaft portion 20 is constant in the present embodiment, but may be changed. The value of the current C input to the drive unit 71 with respect to the revolutions is controlled and changed by the control unit 100 as shown in FIG. 3B. Note that, the revolutions of the shaft portion 20, which is the horizontal axis of the graph shown in FIGS. 3A and 3B, is a value added according to the rotation without distinction (no distinction between positive and negative) of the rotation direction. The control unit 100 rotates the drive unit 71 such that the shaft portion 20 and the breaking member 60 rotate alternately in the positive and negative circumferential directions. Note that, the current C input to the drive unit 71 is proportional to the rotational force (torque) generated by the drive unit 71.

The rotation operation unit 70 and the control unit 100 constitute a rotation controller 101 as shown in FIG. 1. The rotation operation unit 70 and the control unit 100 may be integrally formed in the same housing. Alternatively, the rotation operation unit 70 and the control unit 100 may be configured separately in different housings.

Figure 4:
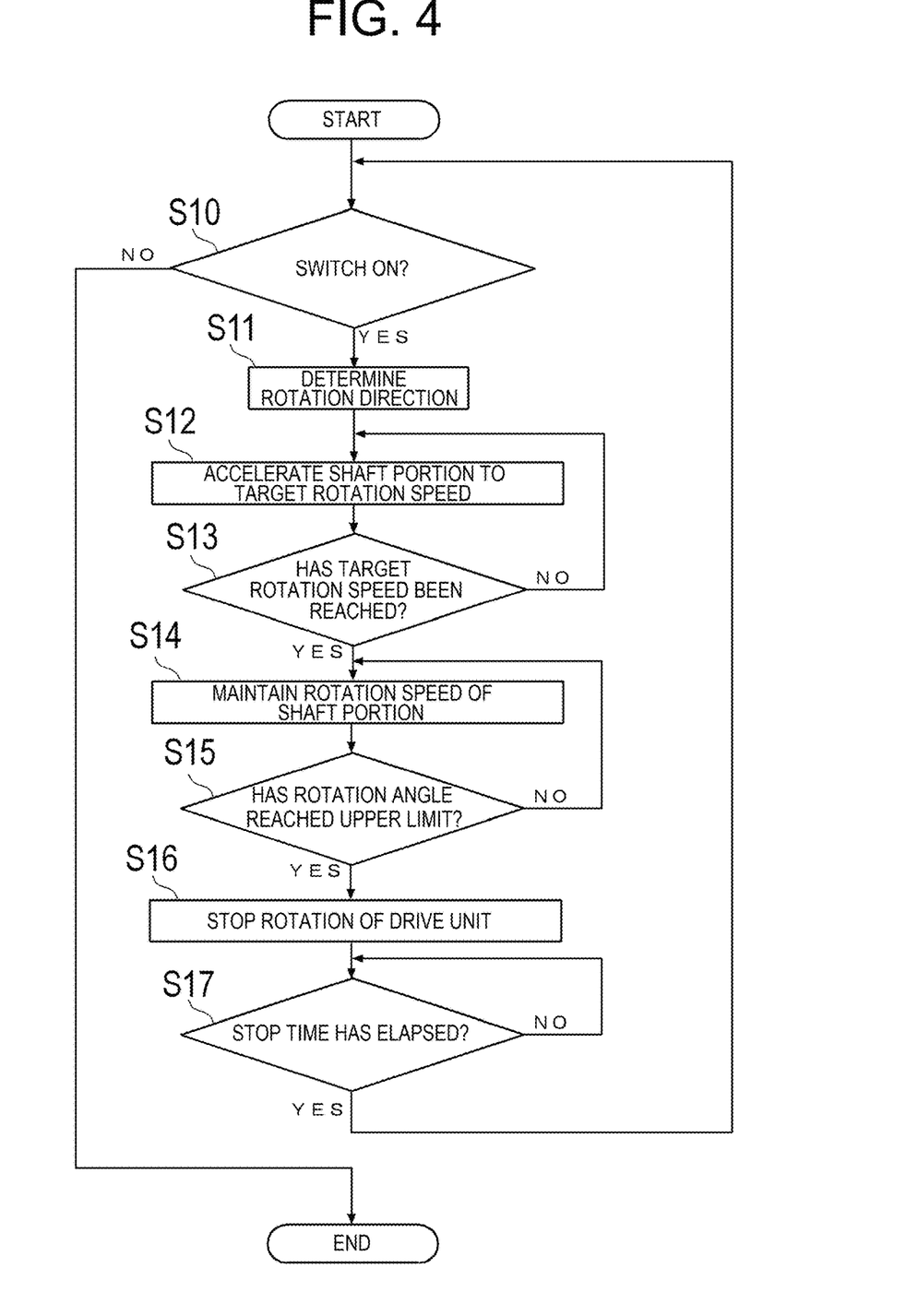
FIG. 4 is a flowchart showing a method for controlling rotation of the medical device.

Next, a method of controlling the rotation of the medical device 10 according to the embodiment will be described as an example of a case where a thrombus in a blood vessel is destroyed and aspirated with reference to the flowchart shown in FIG. 4.

Figure 5A:
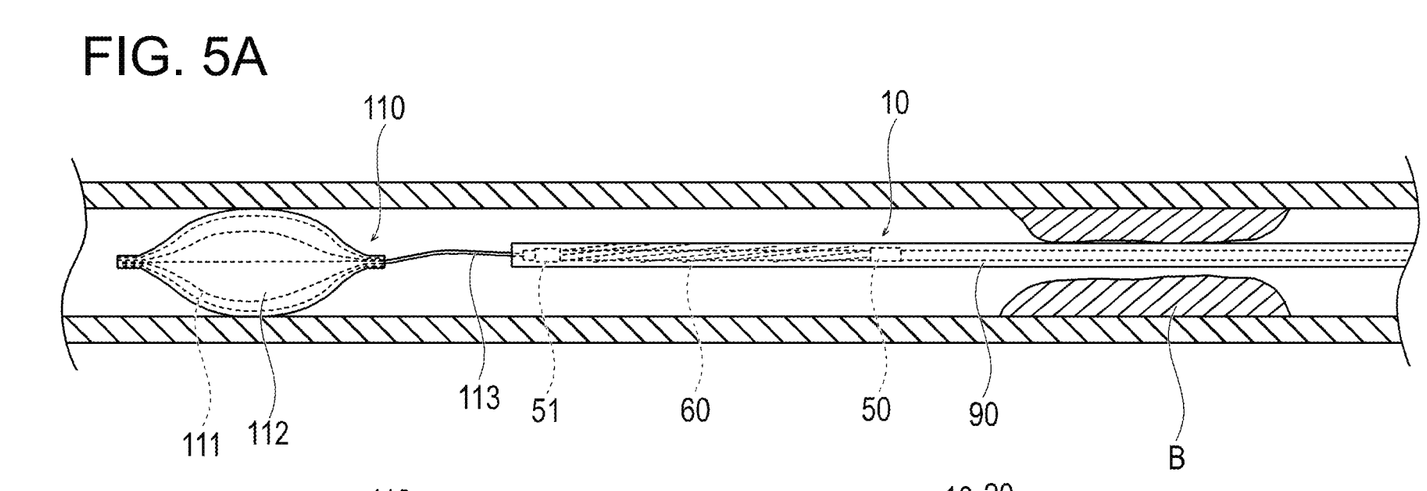

Before inserting the shaft portion 20 of the medical device 10 according to the embodiment, it is desirable that a protective member such as a filter or a balloon that restricts the flow of fluid in the blood vessel be disposed downstream of the thrombus B in the blood vessel (the side to which blood flow is directed). In the present embodiment, as shown in FIG. 5A, a filter device 110 is used which includes an elastic body 111 made of a wire that expands by its own elastic force by being pushed out from a sheath or the like, a mesh-like or membrane-like filter 112 disposed on the outer peripheral surface of the elastic body 111, and a wire portion 113 interlocked with the elastic body 111. When the elastic body 111 pushed out from the sheath or the like expands and the filter 112 comes into contact with a blood vessel, the filter 112 restricts blood flow. Accordingly, the destroyed thrombus B can be prevented from flowing in the blood vessel and moving to another location.

Figure 5B:
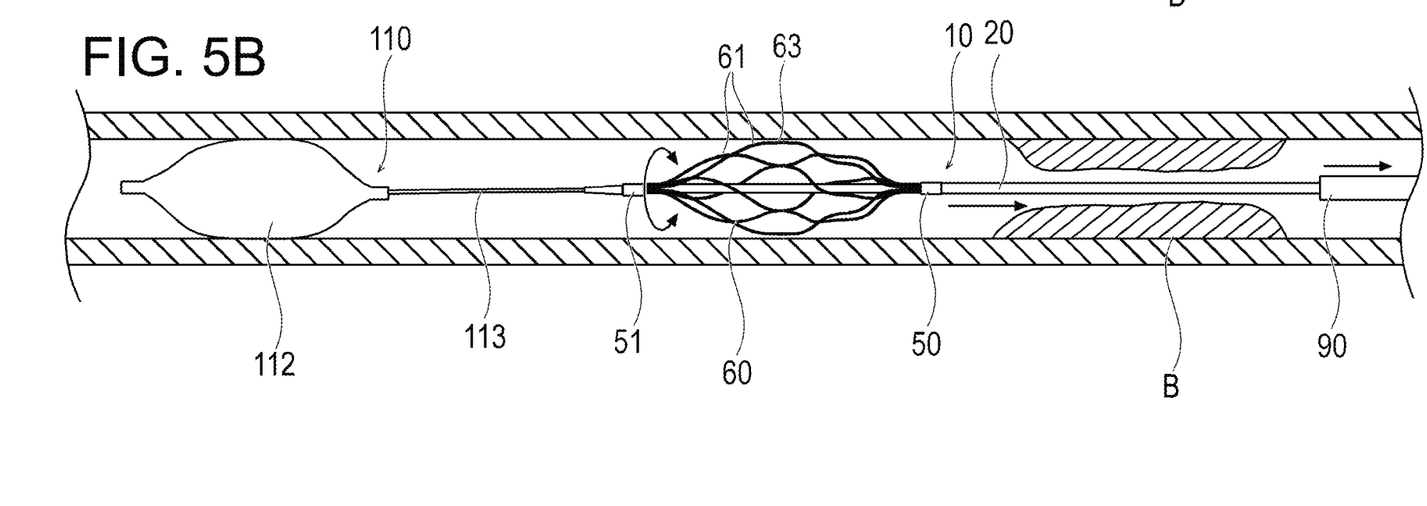

Next, the medical device 10 in a state in which the distal portion of the shaft portion 20 including the breaking member 60 is housed in the outer sheath 90 is prepared. Next, the proximal end portion of the wire portion 113 is inserted into the guide wire lumen of the guide wire pipe body 40 of the medical device 10. Next, the medical device 10 is caused to reach the distal side of the thrombus B using the wire portion 113 as a guide. Thereafter, when the outer sheath 90 is moved to the proximal side with respect to the shaft portion 20, as shown in FIG. 5B, the breaking member 60 is exposed to the outside of the outer sheath 90, and expands by its own elastic force. At this time, the slide portion 50 moves to the distal side with respect to the shaft portion 20.

Next, in a state in which the breaking member 60 is in contact with or close to the thrombus B, the rotation operation unit 70 (see FIG. 1) is operated (step S10). Accordingly, the control unit 100 determines the rotation direction of the drive unit 71 (step S11), and rotates the drive unit 71. Note that, for example, the direction in which the shaft portion 20 is rotated first is the positive direction. The positive and negative in the rotation direction can be reversed. As shown in FIG. 3A, the control unit 100 gradually accelerates the shaft portion 20 and the breaking member 60 driven by the drive unit 71 (step S12). The target rotation speed T is not particularly limited, but is, for example, 2000 rpm (revolutions per minute) to 3200 rpm. When the rotation speed S of the shaft portion 20 reaches the target rotation speed T (step S13), the control unit 100 maintains the rotation speed S of the shaft portion 20 (step S14). The control unit 100 controls the current C input to the drive unit 71 to maintain the target rotation speed T. Since the breaking member 60 that has reached the target rotation speed T has a relatively high speed, it can rather effectively break the thrombus B (i.e., blood clot) stuck to the blood vessel and the thrombus B (i.e., embolism) floating in the blood vessel. Therefore, it is preferable that there is a time during which the breaking member 60 rotates at the target rotation speed T. Note that, it is possible that the breaking member 60 does not reach the target rotation speed T and does not have time rotated at the target rotation speed T.

Figure 6A:
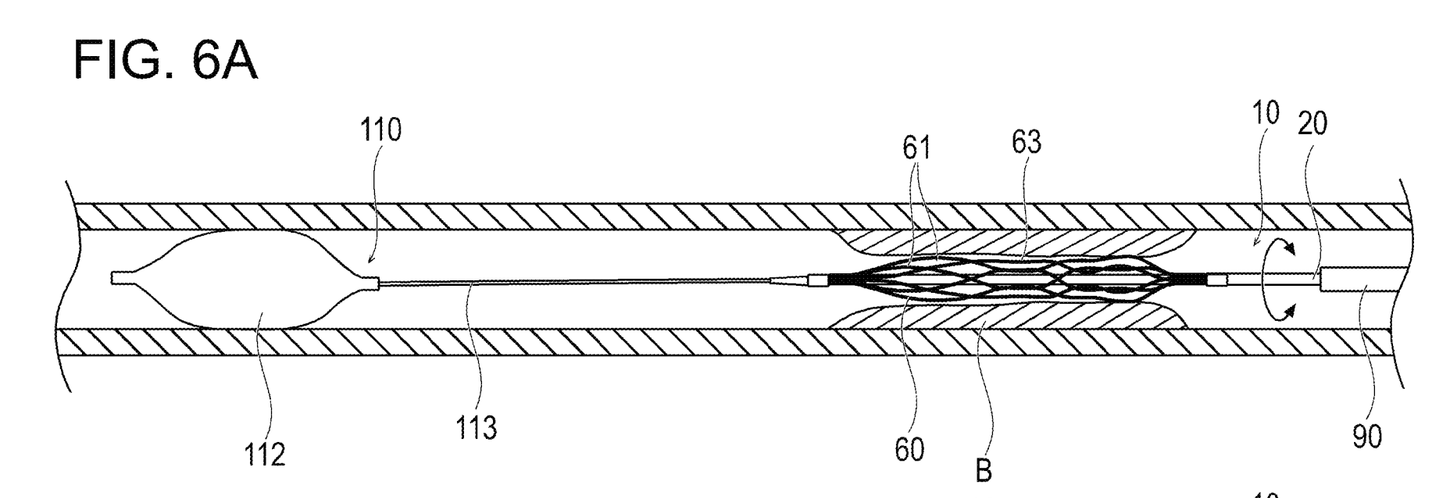
Figure 6B:
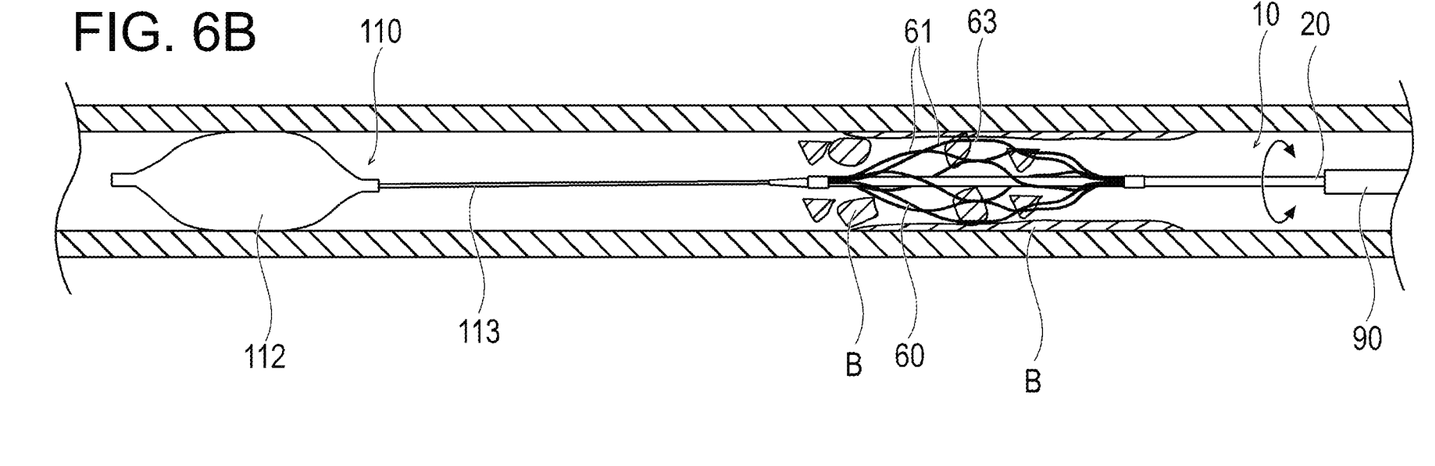

In order to cause the shaft portion 20 and the breaking member 60 to reach the target rotation speed T as quickly as possible, the control unit 100 may set the current C input to the drive unit 71 high at the beginning of rotation as shown in FIG. 3B. When the breaking member 60 rotates in the blood vessel, the breaking member 60 breaks the thrombus B. As shown in FIGS. 6A and 6B, the blood in the blood vessel and the broken thrombus B receive force from the breaking member 60 and rotate. Therefore, the rotation speed of the blood and the thrombus B in the blood vessel rises later than the rotation speed S of the breaking member 60.

When the rotation speed S of the breaking member 60 becomes substantially constant at the target rotation speed T, the blood that is rotated by the force from the breaking member 60 and the broken thrombus B gradually approach the rotation speed S of the breaking member 60, and substantially coincide with each other. That is, the control unit 100 maintains the rotation speed S of the breaking member 60 constant until the rotation speed of the blood and the broken thrombus B substantially coincides with the rotation speed S of the breaking member 60. As the rotation speed of the blood and the broken thrombus B reaches the rotation speed S of the breaking member 60, when the breaking member 60 subsequently rotates in the reverse direction, the relative speeds of the breaking member 60, blood, and the broken thrombus B increase. Therefore, the breaking member 60 can break the thrombus B rather effectively.

When the rotation speed S of the breaking member 60 and the rotation speed of the thrombus B substantially coincide with each other, the thrombus B rotates together with the breaking member 60. Therefore, the breaking member 60 cannot break the thrombus B floating in the blood vessel. Therefore, it is preferable that the rotation of the breaking member 60 be stopped immediately after the rotation speed S of the breaking member 60 and the rotation speed of the thrombus B substantially coincide with each other. The revolutions of the shaft portion 20 and the breaking member 60 in a state in which the rotation speed S of the breaking member 60 and the rotation speed of the thrombus B are substantially the same is not particularly limited, but is preferably, for example, 1 rotation to 5 rotations.

Note that, the condition that the rotation speed S of the breaking member 60 and the rotation speed of the thrombus B are considered to be substantially the same can be set by the rotation angle (revolutions) of the shaft portion 20 and the breaking member 60. For example, when the rotation angle of the shaft portion 20 reaches a predetermined upper limit value (for example, 2880 degrees (8 rotations)) (step S15), the control unit 100 stops the current C supplied to the drive unit 71, and stops the rotation of the drive unit 71 (step S16). Accordingly, as shown in FIG. 3A, the rotation speed S of the shaft portion 20 and the breaking member 60 decreases and becomes zero. It is preferable that the rotation of the shaft portion 20 and the breaking member 60 be stopped promptly so that the rotation can be quickly reversed. By rapidly rotating the breaking member 60 in the reverse direction, the relative speed between the breaking member 60 and the thrombus B increases, and the thrombus B can be broken effectively. The time required for the rotation of the breaking member 60 to stop from the target rotation speed T is preferably shorter than the time required for the rotation of the breaking member 60 to reach the target rotation speed T after the rotation of the breaking member 60 has stopped, but is not limited to this. For example, the rotation speed S of the breaking member 60 may gradually decrease.

When the rotation speed of the blood and the broken thrombus B substantially coincides with the rotation speed S of the breaking member 60, the speed becomes a steady state, and the current C input to the drive unit 71 does not change and becomes substantially constant. Therefore, when the current C input to the drive unit 71 is substantially constant, it can be determined that the rotation speed of the blood and the broken thrombus B substantially coincides with the rotation speed S of the breaking member 60.

The upper limit value of the rotation angle (revolutions) at which the shaft portion 20 and the breaking member 60 are continuously rotated in the same direction, for example, is preferably 720 degrees (2 rotations) or more, more preferably 2880 degrees (8 rotations) or more, still more preferably 5760 degrees (16 rotations) or more. The rotation angle (revolutions) required for the rotation speed S to reach the target rotation speed T from zero is not particularly limited, but is, for example, 2160 (6 rotations). The rotation angle (revolutions) at which the breaking member 60 reaches the target rotation speed T and rotates while being maintained at the target rotation speed T is not particularly limited, but is, for example, 720 degrees (2 rotations).

The breaking member 60 located at the distal portion of the shaft portion 20 has a phase of rotation delayed with respect to the rotation of the drive unit 71 due to the twist of the shaft portion 20. Therefore, after the rotation of the drive unit 71 stops, a predetermined time is required until the rotation of the breaking member 60 stops. Therefore, by providing a stop time during which the rotation of the drive unit 71 is stopped by the control unit 100, the twist of the shaft portion 20 is released, and the breaking member 60 can be restored to a state desired for breaking. Therefore, it is preferable that the stop time of the drive unit 71 is equal to or longer than the time during which the twist of the shaft portion 20 returns. The stop time of the drive unit 71 is preferably shorter than the time required for the rotation of the blood and thrombus B generated by the breaking member 60 in the blood vessel to stop. Accordingly, when the rotation of the shaft portion 20 and the breaking member 60 is resumed, the blood and the thrombus B do not stop and continue to rotate due to the inertial force. Therefore, the relative speed between the breaking member 60 and the floating thrombus B increases, and the breaking member 60 can effectively break the thrombus B. The stop time of the drive unit 71 can be, for example, 0.25 seconds to 0.5 seconds, but is not limited to this, depending on the structure of the shaft portion 20 and the breaking member 60.

Note that, the stop time of the drive unit 71 may be shorter than the time in which the twist of the shaft portion 20 returns. Further, the stop time of the drive unit 71 may not be provided. In these cases, before the twist of the shaft portion 20 returns, the proximal portion of the shaft portion 20 is driven by the drive unit 71 and starts to rotate in the opposite direction. After the proximal portion of the shaft portion 20 starts to rotate, the breaking member 60 located at the distal portion of the shaft portion 20 changes its rotational direction a predetermined time later, and starts to rotate in the same direction as the proximal portion of the shaft portion 20.

When the stop time of the drive unit 71 elapses (step S17), the control unit 100 determines whether the switch 74 is on or off (step S10). If the switch 74 is maintained on, the control unit 100 determines the rotation direction of the drive unit 71 (step S11). The control unit 100 sets the rotation direction of the drive unit 71 to the direction opposite to the rotation direction of the drive unit 71 before the drive unit 71 stops, as shown in FIG. 3A. The control unit 100 gradually accelerates the shaft portion 20 and the breaking member 60 driven by the drive unit 71 to reach the target rotation speed T whose positive and negative direction is opposite to that of the rotation before the stop (step S12). At this time, as shown in FIG. 3B, the current C also has a positive and negative polarity with respect to the case of rotation before the stop. When the breaking member 60 rotates in the blood vessel, the breaking member 60 breaks the thrombus B, as shown in FIGS. 6A and 6B. The blood in the blood vessel and the broken thrombus B receive rotational force from the breaking member 60. At this time, the blood and thrombus B continue to rotate in the positive direction due to the inertial force due to the rotation in the positive direction before the breaking member 60 rotates in the negative direction. Moreover, the rotation speeds of the blood and the thrombus B are accelerated by the breaking member 60 rotating in the positive direction until they substantially coincide with the rotation speed S of the breaking member 60. Therefore, when the breaking member 60 rotates in the opposite direction, the relative difference between the rotation speed S of the breaking member 60 and the rotation speeds of blood and thrombus B increases. Therefore, the shear force acting on the thrombus B floating in the blood vessel is increased by the breaking member 60. Therefore, the thrombus B can be effectively broken by the breaking member 60. When the breaking member 60 rotates in the opposite direction, the maximum shear stress acting between the breaking member 60 and the floating thrombus B can be, for example, 1300 Pa to 3000 Pa, but is not limited to 1300 Pa to 3000 Pa. Thereafter, similarly to the above-described control in the positive direction, when the rotation speed S of the shaft portion 20 reaches the target rotation speed T (step S13), the control unit 100 maintains the rotation speed S of the shaft portion 20 (step S14). Then, when the rotation angle of the shaft portion 20 reaches the predetermined upper limit value (step S15), the control unit 100 stops the current C supplied to the drive unit 71, and stops the rotation of the drive unit 71 (step S16). Next, when the stop time of the drive unit 71 has elapsed (step S17), the control unit 100 returns to the determination of whether the switch 74 is on or off (step S10). Then, as long as switch 74 is maintained on, control unit 100 repeats steps S10 to S17 while changing the rotation direction of drive unit 71. When the switch 74 is turned off by the technician, the control unit 100 maintains the rotation of the drive unit 71 in a stopped state, and ends the control (step S10).

Figure 7A:
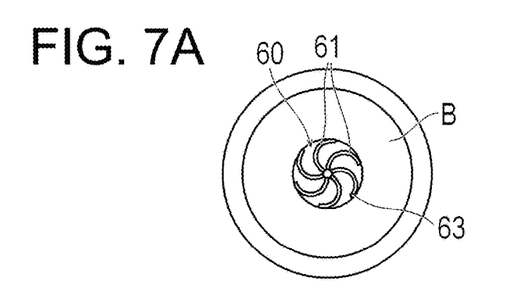
Figure 7B:
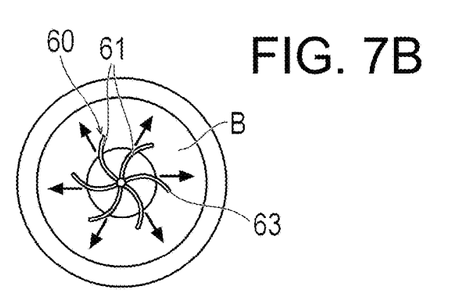
Figure 7C:
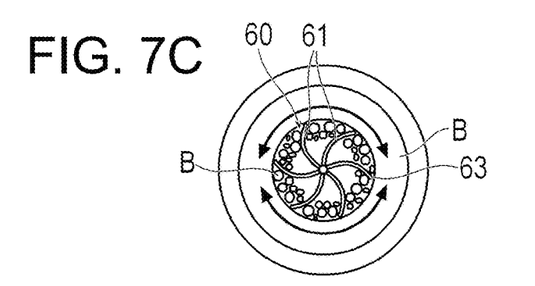
Figure 7D:
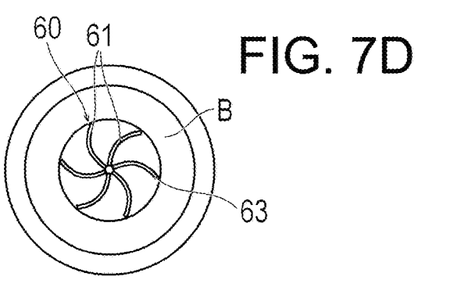

During the operation of the medical device 10, as shown in FIG. 7A, when the rotation is stopped or the speed is reduced to change the rotation direction, the reaction force that the wires 61 receive from the thrombus B decreases. Therefore, the wires 61 spread, and the wires 61 bite into the thrombus B as shown in FIG. 7B. Thereafter, when the wires 61 rotates while being bitten by the thrombus B, the wires 61 scrape the thrombus B, and the thrombus B attached to the blood vessel can be effectively broken, as shown in FIGS. 7C and 7D. The breaking member 60 repeats the operation of biting into the thrombus B when stopped and scraping the thrombus B by the rotation by repeating the rotation and the stop. Accordingly, the breaking member 60 can scrape a large amount of thrombus B rather quickly.

Figure 8A:
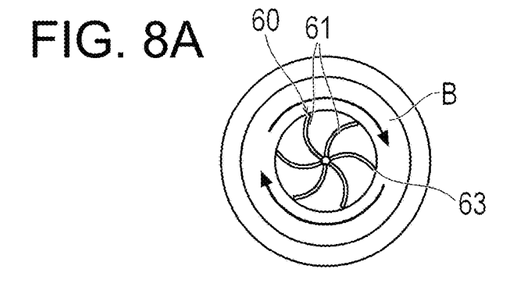
Figure 8B:
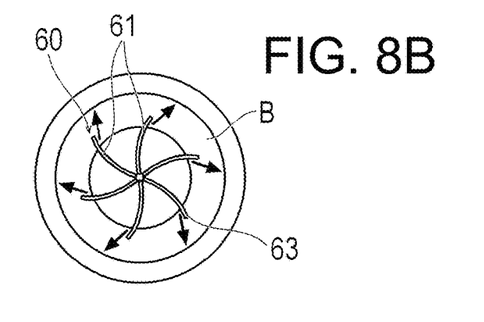
Figure 9A:
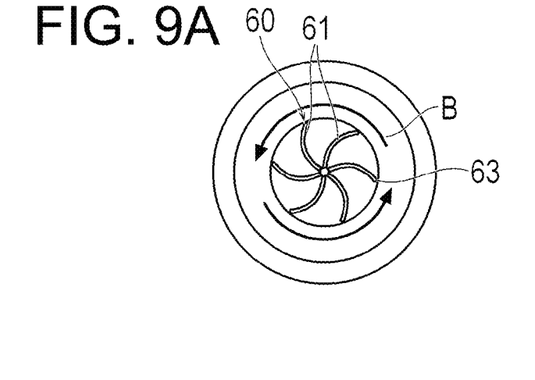
Figure 9B:
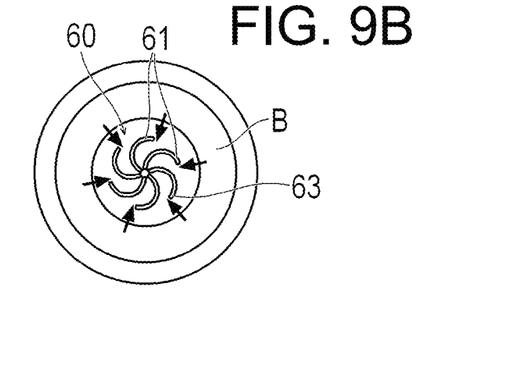

Further, since the projection portion 63 protrudes in the circumferential direction (rotation direction), when the projection portion 63 rotates in the protruding direction as shown in FIG. 8A, the breaking member 60 bites into the thrombus B while expanding as shown in FIG. 8B. By biting, a large amount of thrombus B can be scraped off. Further, since the projection portion 63 protrudes in the circumferential direction (rotation direction), as shown in FIG. 9A, when rotated in the direction opposite to the protruding direction, the breaking member 60 contracts as shown in FIG. 9B. Accordingly, the projection portion 63 can be rather easily separated from the thrombus B, and the breaking member 60 can be rather easily moved in the axial direction. In this way, by repeating the reciprocating rotation of the breaking member 60, it becomes possible to effectively repeat the scraping of the thrombus B and the movement in the axial direction.

By repeatedly reciprocating the breaking member 60 in the axial direction by hand operation while repeating reciprocating rotation of the breaking member 60 by the control unit 100, the thrombus B floating in the blood vessel can be finely broken while the thrombus B attached to the blood vessel is scraped off by the breaking member 60.

When the breaking member 60 is rotated and moved in the axial direction in order to break the thrombus B, the syringe 120 accommodating a thrombolytic agent can be connected to the bypass 91 on the hand-side of the outer sheath 90. Then, simultaneously with the destruction of the thrombus B by the breaking member 60, the plunger of the syringe 120 can be pressed to eject the thrombolytic agent from the distal end portion of the outer sheath 90. The ejection of the thrombolytic agent may be, for example, continuous or intermittent, and the ejection speed and the ejection amount can be desirably changed. In the case where the thrombolytic agent is ejected intermittently, it is possible to aspirate while the ejection is stopped.

By ejecting the thrombolytic agent at the same time as the thrombus B is broken by the breaking member 60, the thrombolytic agent can be rather efficiently soaked into the gap between the thrombus B generated by the breaking effect of the breaking member 60. Therefore, it is possible to soften the thrombus B before destruction, or to reduce the volume of the thrombus B by dissolution. Further, dissolving the broken thrombus B also has the effect of reducing the amount of aspiration for discharging the thrombus B later.

The destroyed thrombus B is stopped by the filter device 110. Thereafter, the plunger of the syringe 120 for aspiration (see FIG. 1) is pulled to bring the inside of the outer sheath 90 into a negative pressure state. Accordingly, the destroyed thrombus B can be aspirated from the opening portion on the distal side of the outer sheath 90 and discharged to the syringe 120 outside the blood vessel.

The aspiration of the thrombus B can be performed either during the rotation of the shaft portion 20 or after the rotation is stopped. After the aspiration of the thrombus B and the stop of the rotation of the shaft portion 20, the breaking member 60 is accommodated in the outer sheath 90, and the medical device 10 is removed from the blood vessel. Thereafter, the filter device 110 is accommodated in a sheath or the like and removed from the blood vessel, and the treatment is completed.

As described above, the medical device 10 according to the embodiment is a device that is inserted into the biological lumen for destroying the thrombus B (object) of the biological lumen, includes a long shaft portion 20 that is rotationally driven, a drive unit 71 that rotates the shaft portion 20, a breaking member 60 that is provided at a distal portion of the shaft portion 20 and is rotatable, and a control unit 100 that controls the rotation of the drive unit 71, in which the control unit 100 controls the drive unit 71 to repeat the rotation while interposing a stop of the rotation between the rotations.

The medical device 10 configured as described above rotates the breaking member 60 while interposing a stop between the rotations. Therefore, it is possible to effectively create a state in which the relative speed between the thrombus B and the breaking member 60, which rotate by receiving the force from the breaking member 60, is large. Therefore, a high shearing stress can be applied to the thrombus B to be destroyed by the breaking member 60, and the thrombus B can be rather effectively broken.

Further, when stopping and rotating the drive unit 71 again, the control unit 100 rotates the drive unit 71 in a direction opposite to the rotation direction before the stop. Accordingly, the relative speed of the thrombus B, which continues to rotate by the inertial force receiving the force from the breaking member 60 before the stop and the breaking member 60 rotating in the opposite direction after the stop, increases. Therefore, the thrombus B can be effectively destroyed by the breaking member 60.

Further, when rotating the drive unit 71 in the opposite direction, the control unit 100 rotates the drive unit 71 at the same rotation angle as a rotation angle of the previous rotation. Accordingly, the thrombus B is prevented from being entangled with the breaking member 60, and the breaking effect can be maintained satisfactorily. Note that, the rotation angles before and after the stop do not have to completely coincide with each other, and may have some fluctuation. The fluctuation of the rotation angle can be, for example, preferably 180 degrees or less, more preferably 90 degrees or less, and further preferably 30 degrees or less.

Further, after stopping the rotation of the drive unit 71, the control unit 100 stops the rotation of the drive unit 71 for a predetermined time. Accordingly, by providing a stop time during which the rotation of the drive unit 71 is stopped, the twist of the shaft portion 20 is released, and the breaking member 60 can be restored to a state desired for breaking.

Further, the control unit 100 continues the rotation of the drive unit 71 in the same direction for 720 degrees (2 rotations) or more. This facilitates rotation of the broken thrombus B following the breaking member 60. Therefore, when the breaking member 60 rotates again after the stop, the relative speed between the thrombus B, which rotates receiving the force from the breaking member 60 and the breaking member 60, increases. Therefore, the thrombus B can be effectively destroyed by the breaking member 60.

Further, the breaking member 60 has the projection portion 63 that is bent in a convex shape radially outward and toward the rotation direction. Accordingly, the projection portion 63 bites into the thrombus B by rotating in the direction in which the projection portion 63 faces, and expands its diameter. By rotating in the opposite direction, the bite of the breaking member 60 is loosened and the diameter of the breaking member 60 is reduced. Therefore, it is possible to effectively repeat the scraping of the thrombus B and the movement of the breaking member 60 in the circumferential and axial directions.

Further, the method for controlling the rotation of the medical device 10 according to the embodiment provided with a long shaft portion 20 that is rotationally driven by a drive unit 71, and a breaking member 60 provided at a distal portion of the shaft portion 20 to destroy a thrombus B (object) in a biological lumen, the method for controlling the rotation of the medical device 10 includes rotating the shaft portion 20 by the drive unit 71, stopping the rotation of the drive unit 71, and rotating the drive unit 71 again.

In the method of controlling the rotation of the medical device 10 configured as described above, the breaking member 60 is rotated while interposing a stop between the rotations. Therefore, it is possible to effectively create a state in which the relative speed between the thrombus B and the breaking member 60, which rotate by receiving the force from the breaking member 60, is relatively large. Therefore, a high shearing stress can be applied to the thrombus B to be destroyed by the breaking member 60, and the thrombus B can be rather effectively broken.

Further, in the present method for controlling the rotation, in the rotation of the drive unit 71 again, the drive unit 71 is rotated in a direction opposite to the rotation direction of the drive unit 71 before the stop. Accordingly, the relative speed of the thrombus B, which continues to rotate by the inertial force receiving the force from the breaking member 60 before the stop and the breaking member 60 rotating in the opposite direction after the stop, increases. Therefore, the thrombus B can be rather effectively destroyed by the breaking member 60.

Further, in the present method for controlling the rotation, in the rotation of the drive unit 71 again, the drive unit 71 is rotated at the same rotation angle as the rotation angle of the previous rotation. Accordingly, the thrombus B is prevented from being entangled with the breaking member 60, and the breaking effect can be satisfactorily maintained.

Further, in the present method for controlling the rotation, after stopping the rotation of the drive unit 71, the rotation of the drive unit 71 is stopped for a predetermined time. Accordingly, by providing a stop time during which the rotation of the drive unit 71 is stopped, the twist of the shaft portion 20 is released, and the breaking member 60 can be restored to a state desired for breaking.

Further, in the present method for controlling the rotation, the rotation of the drive unit 71 is continued in the same direction for 720 degrees (2 rotations) or more, which facilitates rotation of the broken thrombus B following the breaking member 60. Therefore, when the breaking member 60 rotates again after the stop, the relative speed between the thrombus B, which rotates receiving the force from the breaking member 60 and the breaking member 60, increases. Therefore, the thrombus B can be rather effectively destroyed by the breaking member 60.

Further, the present disclosure also provides a procedure method (treatment method) for destroying thrombus B (object) in a biological lumen using the medical device 10 described above. The method is a procedure method for destroying thrombus B in a biological lumen using the medical device 10 provided with a long shaft portion 20 that is rotationally driven by a drive unit 71 and a breaking member 60 provided at a distal portion of the shaft portion 20 to destroy a thrombus B in a biological lumen, the method including delivering the breaking member 60 to the vicinity of the thrombus B by inserting the shaft portion 20 into the biological lumen, rotating the breaking member 60 to destroy the thrombus B while creating a circumferential flow in the biological lumen, stopping the rotation of the breaking member 60, and rotating the breaking member 60 again to destroy the thrombus B while creating a flow in the circumferential direction in the biological lumen.

In the procedure method configured as described above, the breaking member 60 is rotated while interposing a stop between the rotations. Therefore, it is possible to effectively create a state in which the relative speed between the thrombus B which rotates by receiving the force from the breaking member 60 and the breaking member 60, is relatively large. Therefore, a high shearing stress can be applied to the thrombus B to be destroyed by the breaking member 60, and the thrombus B can be rather effectively broken.

Further, in the present procedure method, the direction in which the breaking member 60 is rotated again is the opposite direction to the rotation direction before stopping the rotation of the breaking member 60. Accordingly, the relative speed of the thrombus B, which continues to rotate by the inertial force, receiving the force from the breaking member 60 before the stop, and the breaking member 60 rotating in the opposite direction after the stop, increases. Therefore, the thrombus B can be effectively destroyed by the breaking member 60.

Further, the present disclosure also provides a rotation controller 101 of the medical device 10. The rotation controller 101 is a rotation controller 101 of the medical device 10 provided with the long shaft portion 20 that is rotationally driven, and includes a drive unit 71 that rotates the shaft portion 20, and a control unit 100 that controls the rotation of the drive unit 71, in which the control unit 100 controls the drive unit 71 to repeat the rotation while interposing a stop of the rotation between the rotations.

The rotation controller 101 of the medical device 10 configured as described above can effectively create a state in which the relative speed between the drug such as a thrombolytic agent that rotates by receiving a force from the shaft portion 20 and the shaft portion 20 is relatively large. Therefore, it is possible to create a flow of the drug and enhance the effect of the drug. Further, when the breaking member 60 is fixed to the shaft portion 20, the rotation controller 101 can rather effectively create a state in which the relative speed between the thrombus B, which rotates by receiving a force from the breaking member 60, and the breaking member 60 is relatively large. Therefore, the thrombus B can be rather effectively destroyed by the breaking member 60.

Note that, the present disclosure is not limited to only the above-described embodiments, and various modifications can be made by those skilled in the art within the technical idea of the present disclosure. For example, the biological lumen into which the medical device is inserted is not limited to a blood vessel, and may be, for example, a vessel, a ureter, a bile duct, a fallopian tube, a hepatic duct, or the like. Therefore, the object to be destroyed need not be a thrombus.

Figure 10A:
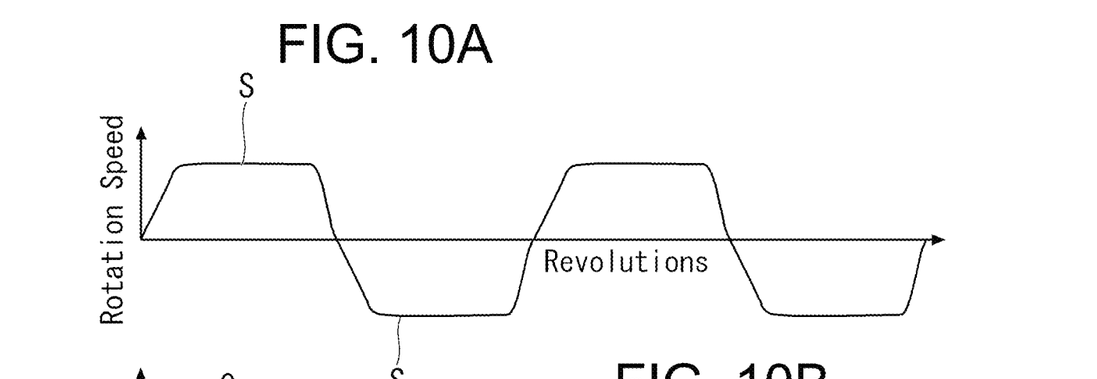
Figure 10B:
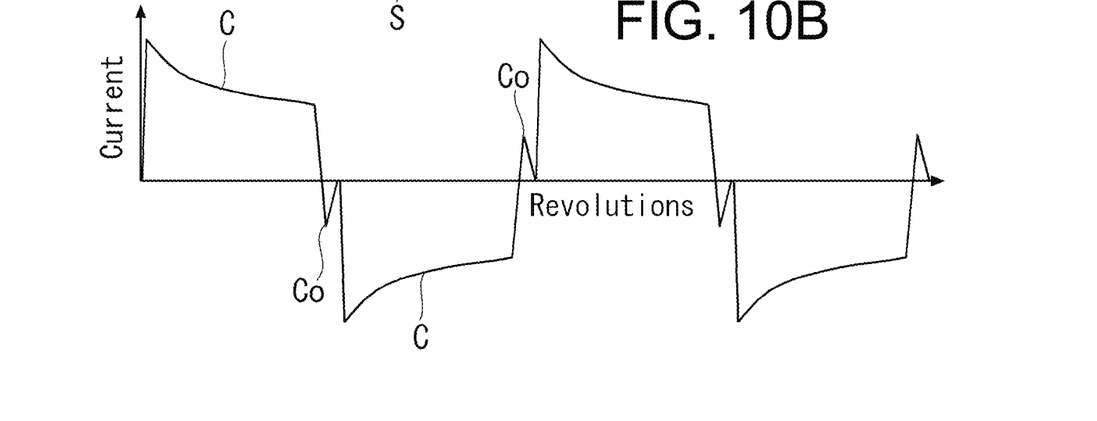

Further, as shown in FIGS. 10A and 10B, when stopping the rotation of the drive unit 71, the control unit 100 may apply the current Co (i.e., a constant current) for generating a rotational force in a direction opposite to the rotation direction to the drive unit 71. Accordingly, the rotation of the breaking member 60 can be rapidly changed, and a state in which the relative speed between the floating thrombus B and the breaking member 60 is large can be effectively created. Therefore, the thrombus B can be rather effectively destroyed by the breaking member 60.

Figure 11A:
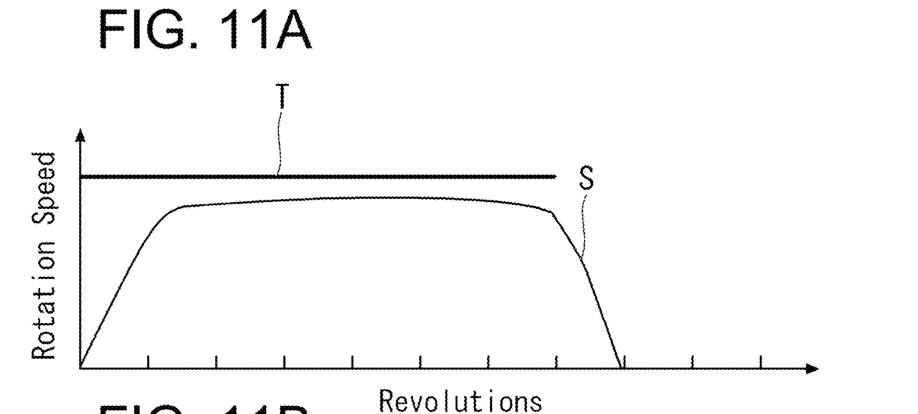
Figure 11B:
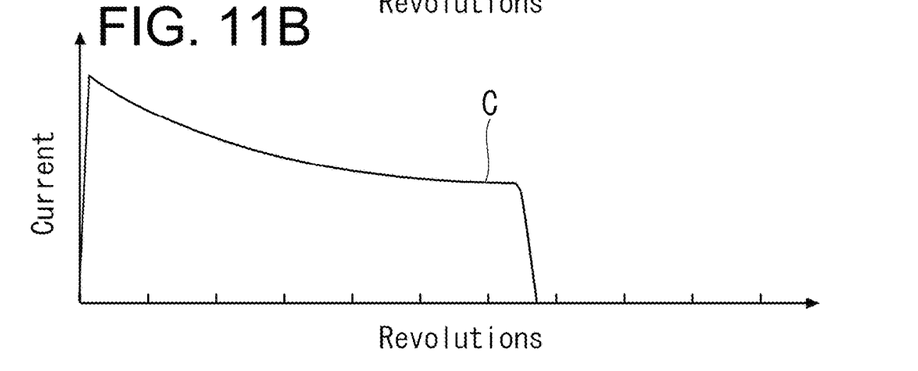

Further, as shown in FIGS. 11A and 11B, the rotation speed S may not reach the target rotation speed T. In this case, for example, the number of times of reversing the rotation of the breaking member 60 within a predetermined time can be increased. Therefore, the thrombus B can be effectively destroyed even if the rotation speed S does not reach the target rotation speed T.

Figure 12A:
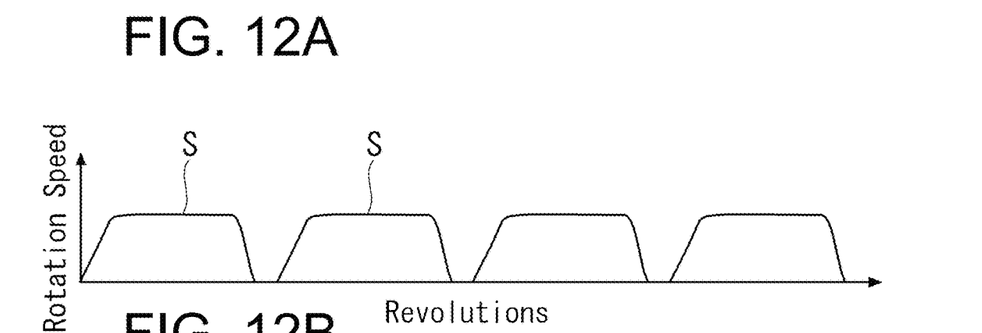
Figure 12B:
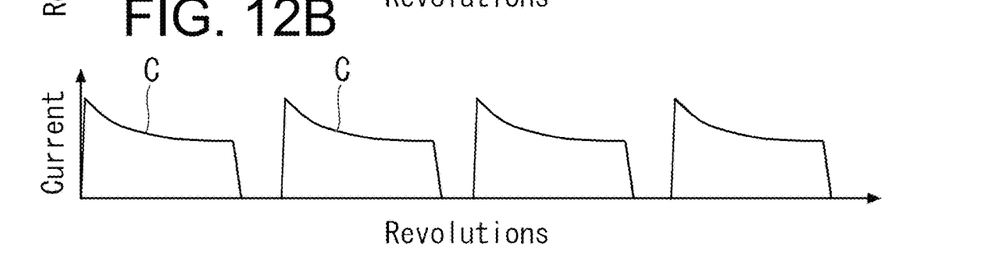

Further, as shown in FIGS. 12A and 12B, the rotation directions of the drive unit 71, the shaft portion 20, and the breaking member 60 may be the same direction instead of the opposite direction with the stop interposed between the rotations. Even in this case, by stopping the rotation of the breaking member 60, the relative speed between the breaking member 60 and the blood and the thrombus B that is broken and floats can be increased. Therefore, the breaking member 60 can effectively destroy the thrombus B.

Further, the wire constituting the breaking member 60 may not be spiral, and may be linear in the axial direction in a circumferential development, for example.

Further, in the present embodiment, the proximal portion of the breaking member 60 can be fixed to the slide portion 50 that can slide with respect to the shaft portion 20, and the distal portion of the breaking member 60 may be fixed to a slide portion slidable with respect to the shaft portion 20.

Further, the control unit 100 may control the value of the current C without specifying the rotation speed S by detection or conversion. By controlling the current C to a value set in advance to obtain a desired rotation speed S, the rotation speed S can be kept within a predetermined range without specifying the rotation speed S.

The detailed description above describes embodiments of a medical device used to destroy an object in a biological lumen, a method for controlling rotation of the medical device, and a rotation controller. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device configured to be inserted into a biological lumen to destroy an object in the biological lumen comprising:
    an elongated shaft configured to be rotationally driven;
    a drive unit configured to rotate the shaft;
    a rotatable breaking member provided at a distal portion of the shaft;
    a control unit configured to control the rotation of the drive unit, and wherein the control unit is configured to control the drive unit to repeat the rotation while interposing a stop of the rotation between rotations of the drive unit; and
    wherein the medical device is configured in such a manner that after stopping the rotation of the drive unit, the control unit is configured to stop the rotation of the drive unit for a predetermined time.

2. The medical device according to claim 1, wherein, when stopping and rotating the drive unit after the stopping of the rotation of the drive unit, the control unit is configured to rotate the drive unit in a direction opposite to a rotation direction before the stop.

3. The medical device according to claim 2, wherein, when rotating the drive unit in the opposite direction, the control unit rotates the drive unit at the same rotation angle as a rotation angle of a previous rotation.

4. The medical device according to claim 1, wherein the control unit causes the rotation of the drive unit to continue in the same direction for 720 degrees or more.

5. The medical device according to claim 1, wherein, when stopping the rotation of the drive unit, the control unit applies a current for generating a rotational force in a direction opposite to a rotation direction to the drive unit.

6. The medical device according to claim 1, wherein the breaking member has a projection portion that is bent in a convex shape radially outward and toward the rotation direction.

7. The medical device according to claim 1, wherein the stopping of the rotation of the drive unit for the predetermined time is in order to release twist of the shaft and restore the breaking member to a desired state for breaking.

8. The medical device according to claim 1, wherein the breaking member includes an expanded state and a contracted state, and the breaking member is configured to destroy the object in the biological lumen in one or more of the contracted state and the expanded state.

9. The medical device according to claim 1, wherein the control unit is configured to control a target rotation speed within 2000 revolutions per minute to 3200 revolutions per minute.

10. A method for controlling rotation of a medical device provided with an elongated shaft that is rotationally driven by a drive unit, and a breaking member provided at a distal portion of the shaft configured to destroy an object in a biological lumen, the method comprising:
rotating the shaft by the drive unit;
stopping the rotation of the drive unit for a predetermined time; and
rotating the drive unit after the stopping of the rotation of the drive unit.

11. The method for controlling rotation of the medical device according to claim 10, wherein the rotation of drive unit after the stopping of the rotation of the drive unit, the method comprises:
rotating the drive unit in a direction opposite to a rotation direction of the drive unit before the stop.

12. The method for controlling rotation of the medical device according to claim 11, wherein the rotation of the drive unit after the stopping of the rotation of the drive unit, the method comprises:
rotating the drive unit at a same rotation angle as a rotation of a previous rotation.

13. The method for controlling rotation of the medical device according to claim 10, comprising:
continuing the rotation of the drive unit in a same direction for 720 degrees or more.

14. The method for controlling rotation of the medical device according to claim 10, wherein when stopping the rotation of the drive unit, the control unit applies a current for generating a rotational force in a direction opposite to a rotation direction to the drive unit.

15. The method for controlling rotation of the medical device according to claim 10, further comprising:
restoring the breaking member to a desired state for breaking by releasing twist of the shaft with the stopping of the rotation of the drive unit for the predetermined time.

16. The method for controlling rotation of the medical device according to claim 15, wherein the breaking member includes an expanded state and a contracted state, further comprising:
destroying the object in the biological lumen in one or more of the contracted state and the expanded state.

17. The method for controlling rotation of the medical device according to claim 15, further comprising:
controlling a target rotation speed within 2000 revolutions per minute to 3200 revolutions per minute.

18. A medical device configured to be inserted into a biological lumen to destroy an object in the biological lumen comprising:
an elongated shaft configured to be rotationally driven;
a drive unit configured to rotate the shaft;
a rotatable breaking member provided at a distal portion of the shaft;
a control unit configured to control the rotation of the drive unit, and wherein the control unit is configured to control the drive unit to repeat the rotation while interposing a stop of the rotation between rotations of the drive unit; and
wherein the control unit is configured to stop the rotation of the drive unit for a predetermined time.

19. The medical device according to claim 18, wherein the control unit is configured to stop the rotation of the drive unit when a rotation angle of the shaft reaches a predetermined upper limit value.

20. The medical device according to claim 18, wherein, when the rotation speed of the breaking member becomes substantially constant at a target rotation speed, the control unit is configured to stop the rotation of the drive unit.

21. The medical device according to claim 18, wherein, when the rotation speed of the breaking member becomes substantially constant at the target rotation speed, the control unit is configured to rotate only 1 rotation to 5 rotations.

22. The medical device according to claim 18, wherein the control unit is configured to control a target rotation speed within 2000 revolutions per minute to 3200 revolutions per minute.

* * * * *